(12) United States Patent
Wyss

(10) Patent No.: US 8,734,396 B2
(45) Date of Patent: May 27, 2014

(54) FLEXIBLE MEDICINE RESERVOIR WITH AN INTERNAL RESERVOIR PORT

(75) Inventor: Martin Wyss, Burgdorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 624 days.

(21) Appl. No.: 12/604,519

(22) Filed: Oct. 23, 2009

(65) Prior Publication Data

US 2010/0228196 A1    Sep. 9, 2010

(30) Foreign Application Priority Data

Oct. 24, 2008  (EP) .................................. 08167548

(51) Int. Cl.
*A61M 5/142* (2006.01)

(52) U.S. Cl.
USPC ........................... 604/151; 604/415; 604/403

(58) Field of Classification Search
USPC ......... 604/407–416, 905, 151, 246, 255, 256, 604/262; 128/DIG. 24
See application file for complete search history.

(56) References Cited

U.S. PATENT DOCUMENTS

| | | | |
|---|---|---|---|
| 3,944,261 A * | 3/1976 | Reed et al. ................... | 285/21.2 |
| 4,632,673 A * | 12/1986 | Tiitola et al. ................. | 604/415 |
| 4,636,412 A * | 1/1987 | Field ............................. | 604/408 |
| 6,394,993 B1 * | 5/2002 | Chang et al. ................. | 604/415 |
| 7,025,754 B2 * | 4/2006 | Proicou et al. ............... | 604/408 |
| 2004/0001655 A1 | 1/2004 | Proicou et al. | |
| 2006/0184119 A1 | 8/2006 | Remde et al. | |
| 2007/0049865 A1 | 3/2007 | Radmer et al. | |
| 2007/0123820 A1 | 5/2007 | Gafner-Geiser et al. | |

FOREIGN PATENT DOCUMENTS

| WO | 2004/009162 A1 | 1/2004 |
| WO | 2008/122135 A1 | 10/2008 |

* cited by examiner

*Primary Examiner* — Laura Bouchelle
(74) *Attorney, Agent, or Firm* — Dinsmore & Shohl LLP

(57) ABSTRACT

Devices for the automatic release of liquid medicaments are disclosed. In particular, a flexible container for storing a liquid medicament, a port for such a flexible container, and a device for the automated release of a liquid medicament are disclosed. A flexible container for storing a medicament comprises sealed top and bottom flexible sheets and at least one port mounted to a wall of the flexible container. The at least one port comprises a flange attached to the wall and an inner conduit connecting the inner storage volume and the exterior of the flexible container. The port comprises an adapter protruding through a hole in the top flexible sheet and a base plate having at least one drain channel connected to the inner conduit via an inner opening on the base plate. A device for the automated release of a medicament comprises at least one flexible container.

19 Claims, 7 Drawing Sheets

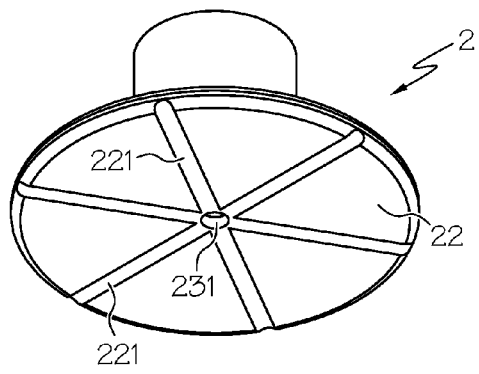
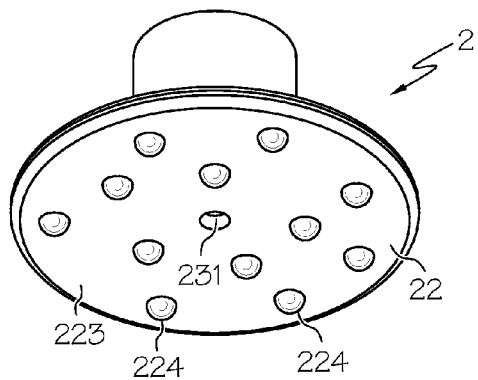
FIG. 3A
FIG. 3B
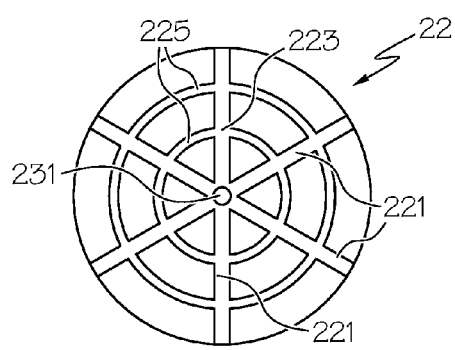
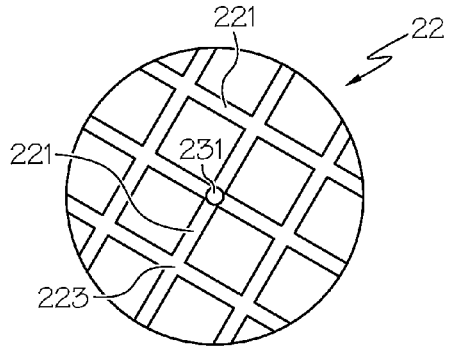
FIG. 3C
FIG. 3D

FLEXIBLE MEDICINE RESERVOIR WITH AN INTERNAL RESERVOIR PORT

CROSS-REFERENCE TO RELATED APPLICATIONS

This application claims the benefit of priority under 35 U.S.C. §119 of European Application No. 08 167 548.0, filed Oct. 24, 2008.

TECHNICAL FIELD

Embodiments of the invention relate generally to devices for the automatic release of liquid medicaments, and in particular to a flexible container for storing a liquid medicament to be administered to a patient by an infusion, to a port for such a flexible container, and to a device for the automated release of a liquid medicament.

BACKGROUND

Devices for the automated release of liquid medicaments normally are used with patients who have a continuous need for a medicine that can be administered by subcutaneous infusion, which need can vary in the course of the day. Example applications for computer-controlled infusion pump devices, such as insulin pumps, include certain pain therapies and the treatment of diabetes. Such devices can be carried by a patient on the body and can contain a certain amount of liquid medicament in a medicine reservoir in the form of a container. The medicine reservoir often comprises medicine sufficient for one or several days. The liquid medicament is supplied to the patient's body from the medicine reservoir through an infusion cannula or an injection needle.

Convenience and discretion are paramount concerns for patients who may self-administer medicaments, for example, insulin, by means such as an infusion pump. Consequently, the dimensions of such infusion devices must be limited, and particularly the overall length should be as small as possible to prevent the devices from being evident through clothing and to allow the patient to carry the devices as comfortably as possible.

In the interest of maintaining sterility and preventing contamination, typically the devices are single-use devices. Alternatively, the devices or parts of the devices can be reused by the patient, for example, by replacing an empty medicament container or by refilling the container. The refilling of containers has the advantage that medicaments that are not readily available in pre-filled containers can be used for such infusion pump devices, thereby providing the patient with a larger choice of sources for delivery of the medicaments.

Standard infusion pump devices that are carried on or near the body have a medicine reservoir with a cylindrical ampoule and a displacement piston. The piston is pushed into the ampoule by a piston rod or a threaded spindle to convey the liquid medicament. These known designs are undesirably long or thick and do not provide advantageously compact infusion pumps.

Manufacturers try to meet the demand of small infusion pump devices by various means. For example, the infusion pump can be divided into structural assemblies arranged in separate, smaller housings that can joined by a wireless or a wired connection. An example of such a modular infusion pump device is disclosed in U.S. 2006/0184119 A1.

Another possibility is the use of particularly flat containers. For example, the cylindrical ampoule may be replaced by a container having a rectangular or other suitable cross-section and may interact with a displacement piston of a corresponding shape. Different embodiments of such compact medicine reservoir devices are shown in WO 2008/122135 A1.

A further approach to reduce the overall volume of an infusion device is to replace the syringe-type dosing mechanism with a downstream pump system. In the syringe-type dosing mechanism, an actuator displaces a piston along a long axis of a container to convey the appropriate amount of liquid medicine. In the device with a downstream pump system, a miniaturized pump downstream of the reservoir causes a negative pressure-gradient that conveys the product from the reservoir to its destination. An example of such a pump is described in WO 2004/009162 A1.

For some of the abovementioned infusion devices, the pressure gradient achievable with the pump system is not very high. A suitable container for such devices is disclosed in U.S. 2007/0123820 A1, comprising a flat container and a flat piston body arranged in the body in a sliding manner. Fully filled, such a container has a ratio of maximum height to overall width of less than 1.25. The cross-sectional area of the container in relation to the displacement axis is much larger than for conventional cylinder-piston arrangements. Even a comparably small pressure gradient generated by a miniaturized pump can overcome the friction force of the piston seal as the piston glides on the inner wall of the container.

In an especially advantageous approach the rigid container and movable piston are replaced by a flexible container. Such a flexible container may comprise, for example, two flexible-wall sheets that are sealed together.

One type of infusion pump device with a flexible container is disclosed in U.S. 2007/0049865 A1. The flexible container comprises a front and rear wall sheet sealed together, and a port that is centrally arranged on one of the wall sheets. The port comprises a septum and a flange sealed onto the sheet material. A hollow needle penetrates the septum, thereby connecting the container to the infusion cannula. The flexible container containing the liquid medicament is arranged in a second, rigid, fluid-filled container in fluid communication with a primary reservoir of a hydraulic fluid through a conduit comprising a flow restrictor. The primary reservoir is essentially a cartridge with a moveable piston. A spring is arranged to act on the piston to drive fluid from the reservoir to the second container, thereby expelling medicament from the flexible container when the latter is connected to an infusion needle. The flow rate is determined by the pressure generated in the drive fluid, the viscosity of the drive fluid, and the flow resistance in the flow restrictor. Because the contained cannot be refilled, the device is intended for single use. Also, both the hydraulic fluid piston and the second, rigid container increase the total volume of the device. Furthermore, the indirect pumping method complicates the construction of the device and limits the dosing accuracy. Such an infusion pump device thus is not suitable for dosing-critical applications such as the administration of insulin to a diabetes patient.

A common problem of flexible containers with ports as used, for example, in IV bags, is the dead volume resulting between the collapsed container and the port. Dead volume cannot be used, meaning that it cannot be emptied. Thus, flexible containers are impossible to completely drain. Though dead volumes are of minor concern for larger flexible containers of 100 mL or more, such as those used, for example, for blood preservations, nutritional fluids, or intravenous infusions, the loss of useable container volume is of considerably higher concern with smaller containers suitable for infusion pumps having a total volume of only 5 mL or less. In addition, the concentration of the medicament may be much higher than in an intravenous solution container, which further increases the negative effect of the dead volume. In addition to the increased costs, the dead volume leads also to an increase of the overall volume of the flexible container, and thus of the volume of an infusion pump device comprising such a flexible container.

For single-use containers filled with the medicament, the dead volume increases the effective costs per dose and thus of the overall therapy costs, because a certain percentage of the medicament inevitably will remain in the container and will be wasted. This cost effect is especially important for expensive medicaments.

If a container is provided empty, intended to be filled with the appropriate medicament by the user, the dead volume initially is filled with air. If the air remains in the container it may lead to potentially dangerous dosing errors. Furthermore, the administration of air into a patient's body should be avoided in some applications for medical reasons. However, removing the air from the container requires a certain skill of a user.

Another problem of flexible containers is the possibility that the container does not collapse homogeneously. Because the inner sides of the two wall sheets are pressed together by a pressure difference, parts of the container may be cut off from the port. Such constrictions are particularly problematic for very flexible materials with low elasticity. Other factors influencing the collapsing behavior of flexible containers include the shape and the size of a container, and the position of the port on the container.

Thus, there remains an ongoing need for improved flexible containers for storing medicaments.

SUMMARY

Devices for the automatic release of liquid medicaments are disclosed. In particular, a flexible container for storing a liquid medicament, a port for such a flexible container, and a device for the automated release of a liquid medicament are disclosed.

In one embodiment a flexible container for storing a medicament is disclosed. The flexible container comprises a top flexible sheet having at least one port hole defined therethrough; a bottom flexible sheet sealed to the top flexible sheet so as to form an inner storage volume between the top flexible sheet and the bottom flexible sheet; and at least one port having: a flange that is sealingly attached to an inner side of the top flexible sheet, thereby mounting the port only to the inner side of the top flexible sheet, an adapter for connecting the port to a device and having an outer opening defined therein, the adapter extending from the flange so as to protrude through the at least one port hole in the top flexible sheet, a base plate facing the inner storage volume and having an inner opening and at least one drain channel defined therein, the inner opening being disposed within the at least one drain channel, and an inner conduit defined therein extending from the inner opening to the outer opening so as to provide a fluid connection between the inner storage volume and the outer opening via the inner opening.

In further embodiments, a port for a flexible container that is used with a device and has walls for storing a medicament therebetween is disclosed. The port comprises a flange which connects to an inner side of one of the walls; an adapter for connecting to the device and having an outer opening defined therein, the adapter extending perpendicularly from the flange; and a base plate extending from the flange and having an inner opening and at least one drain channel defined therein, the inner opening being disposed within the at least one drain channel, wherein the port has an inner conduit defined therein extending from the inner opening to the outer opening.

In still further embodiments, a device for the automated release of a liquid medicament may comprise at least one flexible container according to another embodiment. The device may comprise an infusion pump, for example.

These and other features, aspects, and advantages of the present invention will become better understood with reference to the following description, appended claims, and accompanying drawings.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings of non-limiting, example embodiments, in which:

FIGS. 1A-1C schematically show an embodiment of a flexible container, wherein FIG. 1A is a perspective view, FIG. 1B is a cross-sectional view, and FIG. 1C is an enlarged detail view of the cross-section in FIG. 1B;

FIGS. 2A-2B schematically show the embodiment of the port shown in FIG. 1C, wherein FIG. 2A is a cross-sectional view, FIG. 2B is a perspective view onto the base plate.

FIGS. 3A-3D schematically show four embodiments of drain channel arrangements for ports, wherein FIGS. 3A and 3B are perspective views, and FIGS. 3C and 3D are views onto the base plate;

FIGS. 4A-4B schematically show a cross-section of a further embodiment of a flexible container, wherein FIG. 4A shows the flexible container in a completely empty state, and FIG. 4B shows the flexible container in a fully filled state;

DETAILED DESCRIPTION

Figure 1A:
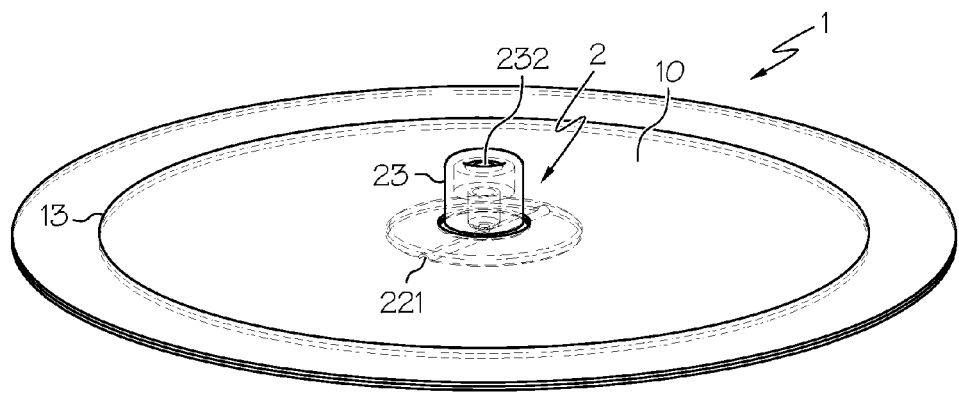

Features and advantages of the invention now will be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "medicament" and "liquid medicament" are meant to encompass any drug-containing flowable medicine, or therapeutic or diagnostic liquid, capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In particular the term medicament encompasses insulin preparations ready for administration.

The terms "subcutaneous infusion" and "subcutaneous injection" are meant to encompass any method in which a needle device is inserted at a selected site within the body of a patient for subcutaneous, intravenous, intramuscular, or intradermal delivery of a liquid medicament to a subject. Further, the term needle defines a piercing member (including an array of micro-needles) adapted to be introduced into or through the skin of a subject.

The terms "drain channel" and "drain channel network" are meant to encompass any arrangement of depressions and protrusions on a surface that provide space between the surface and a flexible sheet firmly abutted to the surface, such that the space is sufficiently interconnected to permit fluid to flow through the space.

In example embodiments, a flexible container for storing a medicament comprises a top flexible sheet and a bottom flexible sheet sealed to the top flexible sheet. Thus, the top flexible sheet and the bottom flexible sheet together compose an outer wall of the flexible container. An inner storage volume is disposed between the top flexible sheet and the bottom flexible sheet. The flexible container has the advantage of a small volume surplus in relation to the content of the flexible container. This in turn reduces manufacturing costs and decreases the dimensions of an infusion pump device comprising such a flexible container. In example embodiments, the inner storage volume of a flexible container for use in a infusion pump device may be up to 10 mL, alternatively 5 mL or less, alternatively 1.5 mL to 3.5 mL.

The top flexible sheet and the bottom flexible sheet each can be a monolayer film or a multilayer structure. Each may comprise one or more polymers of the following families: Polypropylene (PP), Polyethylene (PE), and copolymers; Ethylene Vinyl Acetate (EVA), Polyvinyl Chloride (PVC), Polyvinylidene Chloride (PVDC), Polystyrene (PS), Ethylene Vinyl Alcohol (EVOH), Polyethylene Terephthalate (PET), Polyamide (PA), Polychlorotrifluoroethylene (PCTFE), Cyclic Olefin Copolymer (COC), Thermoplastic Elastomer (TPE), or generally any other polymer material which is known to the skilled person to be suitable for such a purpose.

The outer wall of the flexible container may be manufactured for example by extrusion, blown film extrusion, coextrusion or lamination. If the outer wall comprises a multilayer structure, during production of the structure one or more tie layers may be included, or one or more adhesive layers may be applied between the functional layers. In example embodiments, a metalized film or a silicon oxide or aluminum oxide coating may be applied to improve barrier properties.

The sealing of the top flexible sheet and the bottom flexible sheet may be achieved by methods such as, for example, heat sealing, ultrasonic welding, high-frequency inductive welding, gluing, or any other suitable method for producing flexible containers from sheet-like material that is known to the skilled person. The sealing may be made about a sealing rim. The flexible sheets may comprise a single layer foil of a suitable polymer, or a foil having a multilayer structure. The sealed flexible sheets define together a base area of the flexible container. The base area may have any suitable shape such as, for example, that of a square, a rectangle, a circle, an oval, or a hexagon. In some embodiments, the shape of the base area may be adapted to a specific infusion pump device.

In some embodiments, the top flexible sheet and the bottom flexible sheet are not separate sheets. Rather, the outer walls of the container may be produced from a single flexible sheet that is folded along an axis, and is sealed along the remaining edges. In further embodiments, continuous-film tubes may be utilized to produce the outer walls of the flexible container.

The flexible container further comprises at least one port mounted in the top flexible sheet for transferring the medicament into or out of the inner storage volume. Medicament transferred out of the flexible container may be administered to a patient, for example, by means of an infusion pump device. The at least one port comprises a flange that is sealingly attached to the top flexible sheet, an inner conduit, a base plate facing the inner storage volume, and at least one drain channel disposed within the base plate. The inner conduit defined within the port extends from an inner opening defined in the base plate and an outer opening defined by the adapter. The inner conduit is configured to provide a fluid connection between the inner storage volume and the outer opening (and, thereby, the exterior of the flexible container) via the inner opening. The inner opening is disposed within the at least one drain channel. In some embodiments, the inner conduit may be an integral part of the inner opening such as, for example, by being formed by the same bore or hole.

In example embodiments, the port may comprise a polymer of the following families: Polypropylene (PP), Polyethylene (PE), and copolymers; Ethylene Vinyl Acetate (EVA), Polyvinyl Chloride (PVC), mixtures thereof, or generally any other suitable polymer material. In some embodiments, depending on the process used to attach the port to the wall of the container, the port and the adjacent layer of the outer wall comprise materials of the same polymer family.

In one example embodiment the flange of the at least one port may be arranged in a depression on an inner side of the outer wall. In further example embodiments, the shape of the base plate may be tailored such that the base plate and the adjacent area of the inner side of the outer wall form an essentially flat and smooth surface. As used here, an essentially flat and smooth surface is characterized by a lack of gaps or protrusions at the interface of the base plate and the adjacent area. The flange may be attached to the container wall by common techniques such as, for example, heat sealing, ultrasonic welding, high-frequency inductive welding, gluing, or any other suitable technique. Positioning the flange inside the flexible container enables pressure inside the flexible container to press the flange against the outer wall, thereby reinforcing the sealing of the port of the flexible container. In embodiments wherein the flexible sheets comprise a compound foil, no contact exists between outer foil layers and the content of the container.

In an alternative embodiment, the flange of the port may be attached to an outer side of the outer wall of the flexible container instead of being attached to the inner side of the outer wall. Thereby, only the part of the base plate not being part of the flange will face the inner volume of the container. As such, the port can be mounted in a simpler manner, because the adapter of the port need not be positioned in a hole of the outer wall, but may be simply placed on the hole. Furthermore, detrimental dead volume can be reduced, and the flexible container can be flattened completely when emptied.

The at least one port comprises a base plate facing toward the interior of the container. One or more drain channels are arranged on the base plate and are connected to the inner conduit of the port via an inner opening located on the base plate. The drain channels enable fluid remaining in the flexible container to flow to the inner conduit even if the container is collapsed and the base plate firmly abuts the outer wall. In some embodiments, the base plate may comprise a network of interconnected drain channels.

To minimize dead volume, the drain channels should be as shallow as possible. Among other factors, the minimum achievable drain channel depth that avoids blocking of the channels for a given channel network depends on the flexibility of the flexible sheets and the width of the channels. Furthermore, a minimum flow must be ensured, as determined, for example, by the demands of the dosing pump and the viscosity of the liquid medicament.

In one embodiment, the drain channel network of the base plate of the port extends to the outer walls of the flexible container. Such a drain channel network can be manufactured, for example, by hot embossing a grid of lines on at least a part of the inner surface of the outer wall, such as on either or both of the flexible sheets. In such an embodiment the drain channels of the port are connected to the embossed grid line network. No portion of the content can be blocked and separated from the port when the container collapses in a suboptimal manner during emptying, because the liquid can always flow to the port through the grid line network. This is true even for very large flexible containers and for flexible containers having especially flexible outer walls In example embodiments a circumferential channel may be arranged along the edge of the base plate, facing toward the sealing rim. The circumferential channel can improve the connection between the surrounding remaining container volume and even one single drain channel.

In further embodiments the port may comprise functional elements such as, for example, a bubble filter in the inner conduit, a pressure sensor, a pressure-transfer membrane for coupling the inner conduit to a pressure sensor, or any combination of these. The port also may comprise a pumping mechanism or a part of a pumping mechanism, for example, a micro-membrane pump or a micro-plunger pump.

Figure 1B:
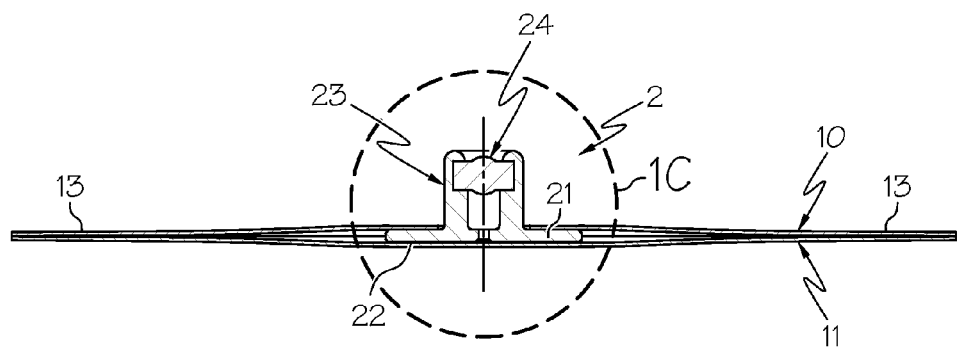
Figure 1C:
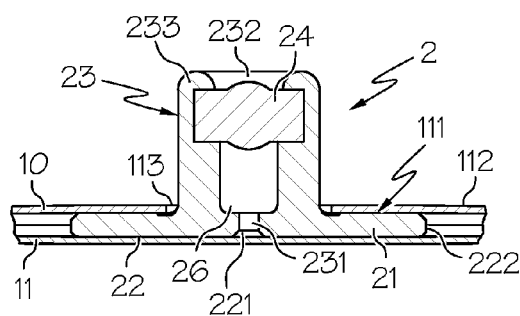

An example embodiment of a flexible container 1 is shown in FIGS. 1A-1C. The flexible container 1 is shown empty and, by way of illustration and not for limitation, as essentially circular. A top flexible sheet 10 and a bottom flexible sheet 11, each comprising a flexible material impervious to liquid, together compose the outer wall and external surface of the flexible container 1. The top flexible sheet 10 and the bottom flexible sheet 11 are sealed around the circumference of the flexible container 1 by a sealing rim 13.

A port 2 is disposed in the center of the top flexible sheet 10. The port 2 comprises a flange 21 for mounting the port 2 on at least one of the top flexible sheet 10 and the bottom flexible sheet 11. The port 2 further comprises an adapter 23 for connecting the port 2 to an infusion pump device (not shown), or to a device (not shown) such as a device for filling or refilling the flexible container 1 such as by transferring medicament into or out of an inner storage volume between the top flexible sheet 10 and the bottom flexible sheet 11. The port 2 further comprises a base plate 22 facing the volume of the flexible container 1 between the top flexible sheet 10 and the bottom flexible sheet 11. The base plate 22 adjoins with the flange 21 and with a longitudinal end of the adapter 23, such that the base plate 22 faces toward the bottom flexible sheet 11. Thus, in the example embodiment shown, particularly as evident from FIGS. 1C, 2A, and 2C, the flange 21, the adapter 23, and the base plate 22 are integral to each other, such that the port 2 is a unitary piece formed from a single continuous piece of material. An inner conduit 26 is defined within the port 2 and leads from an outer opening 232 defined by the adapter 23 to an inner opening 231 defined by the base plate 22, the inner opening 231 being disposed in the center of the base plate 22.

In the example embodiment shown, a septum 24 is disposed in the inner conduit 26. The septum 24 is held within the inner conduit 26 by an upper edge 233 of the adapter 23 that has been deformed inwardly. The septum 24 may comprise any material able to reseal after being penetrated by an object such as a hollow needle. For example, the septum 24 may comprise a silicone polymer. The septum 24 enables the flexible container 1 to be connected, for example, to an outer conduit system for transferring a liquid medicament into and out of the flexible container 1. The flange 21 of the port 2 is connected in a liquid-tight manner (i.e., sealingly attached) to the inner side 111 of the top flexible sheet 10 by suitable means such as, for example, by ultrasonic welding. As is clearly shown in FIGS. 4A and 4B, the sealing attachment of the flange 21 to the inner side 111 of the top flexible sheet 10 is the only means by which the port 2 is mounted within the flexible container 1. The adapter 23 protrudes through a port hole 113 in the top flexible sheet 10 of the flexible container 1.

Figure 2A:
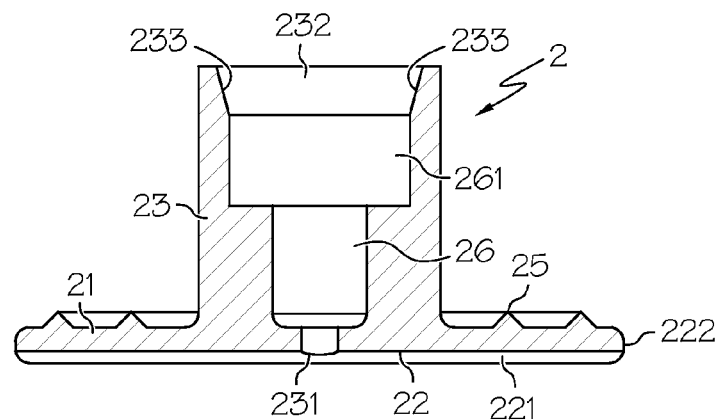
Figure 2B:
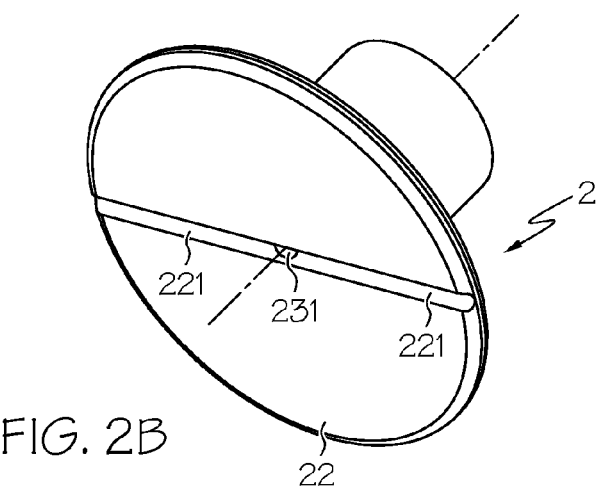
Figure 2C:
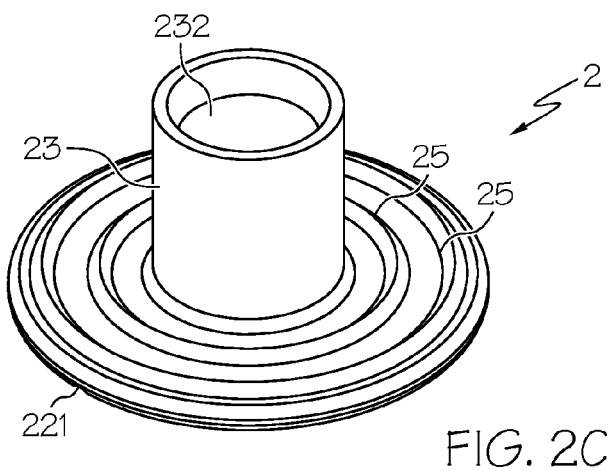
FIG. 2C is a perspective onto the flange and the adapter.

The port 2 is shown in greater detail through the embodiments depicted in FIGS. 2A-2C. A drain channel 221 is arranged across the diameter of the base plate 22, and the inner opening 231 opens out into the drain channel 221. Because the drain channel 221 runs in the plane of the view shown in FIG. 2A (i.e., parallel to the viewing axis of FIG. 1B), only the cross-section of the drain channel 221 is visible in FIG. 2A. However, the configuration of the drain channel 221 is clearly visible in the perspective view shown in FIG. 2B.

The port 2 depicted in FIGS. 2A-2C is shown without a septum. After the port 2 is manufactured, for example by injection molding, a septum may be placed within in the broader upper area 261 of the inner conduit 26. Then, the upper edge 233 of the adapter 23 may be inwardly deformed, for example by a thermal deformation, to grip the septum. In FIGS. 2A and 2C energy directors 25 for ultrasonic welding are shown, circumferentially arranged on the flange 21.

Referring back to FIGS. 1A-1C, when the liquid contents of the flexible container 1 are removed during use, for example during use of an infusion pump device, the pressure in the inner storage volume decreases relative to the ambient pressure against the exterior of the flexible container. The resulting pressure difference causes the top flexible sheet 10 and the bottom flexible sheet 11 to collapse. During the emptying of the flexible container 1, the top flexible sheet 10 and the bottom flexible sheet 11 begin to touch each other. The touching of the top flexible sheet 10 and the bottom flexible sheet 11 may begin at the sealing rim 13, but also may begin at a different location. Where the touching begins depends on factors such as the elasticity of the top flexible sheet 10 and the bottom flexible sheet 11 and also the orientation of the flexible container 1 with respect to gravity. Because the base plate 22 has a non-zero height, when the base plate 22 finally touches the bottom flexible sheet 11, there still remains a certain distance between the top flexible sheet 10 and the bottom flexible sheet 11 under an adjacent area 112 of the inner side 111 of the top flexible sheet 10 with respect to the edge 222 of the base plate 22. The liquid disposed within this last remaining volume then may flow through the drain channel 221 into the inner conduit 26, until the flexible container 1 is completely drained and collapsed. In reverse, if liquid is pumped into a flexible container 1 that is completely empty, with the top flexible sheet 10 and the bottom flexible sheet 11 completely touching each other, the liquid is distributed via the drain channel 221, and the top flexible sheet 10 and bottom flexible sheet 11 are separated in a controlled manner.

Further example embodiments of arrangements of drain channels 221 within the port 2 of the flexible container 1 are shown in FIGS. 3A-3D. The example embodiment shown in FIG. 3A comprises a port 2 with a base plate 22 on which three drain channels 221 are arranged in a star-like manner. In the example embodiment shown in FIG. 3B a plurality of protrusions 224 are arranged on the base plate 22, such that spaces between the plurality of protrusions 224 form the drain channel network 223. In the example embodiment shown in FIG. 3C, the drain channel network 223 arranged on the base plate 22 comprises three drain channels 221 interconnected by two circular drain channels 225. In the embodiment shown in FIG. 3D, the drain channel network 223 comprises drain channels 221 configured in a grid-like arrangement.

Figure 4A:
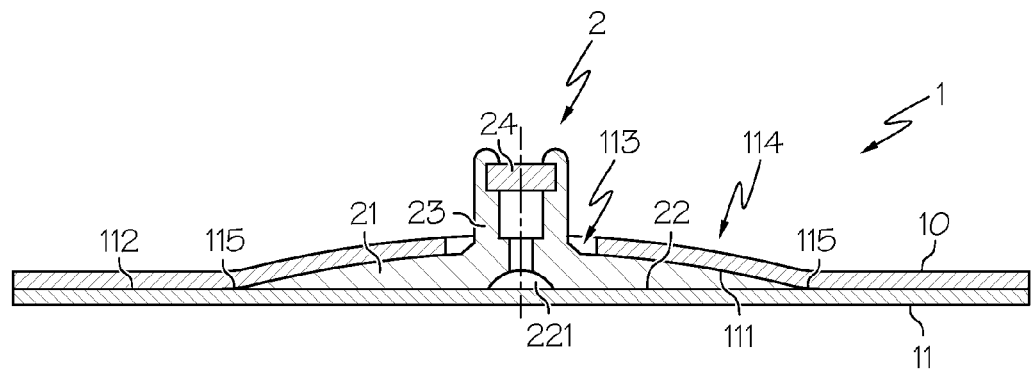
Figure 4B:
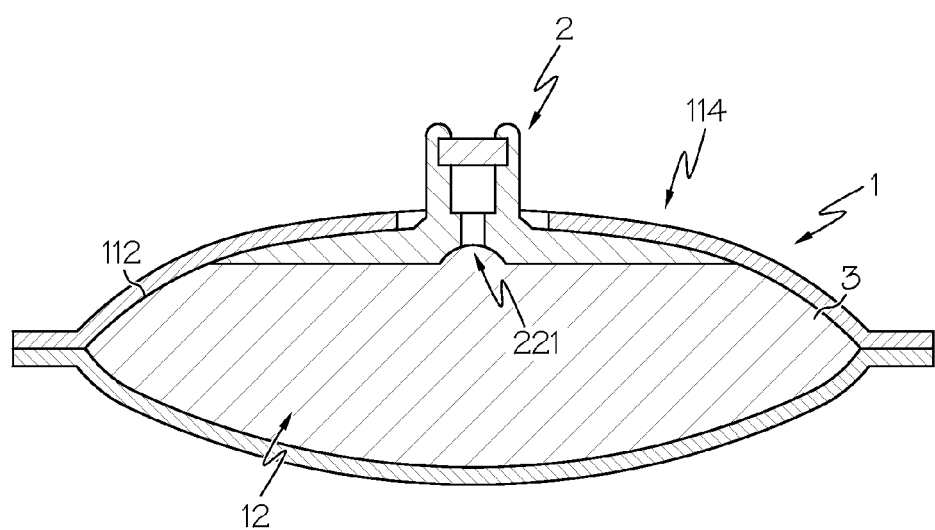

Another embodiment of a flexible container 1 is shown in FIGS. 4A and 4B. FIG. 4A shows the flexible container 1 in a drained state, and FIG. 4B shows the flexible container in a filled state, wherein the inner storage volume 12 is filled, for example, with a liquid medicament 3. In both figures the cross-section of the flexible container 1 is perpendicular to the axis of the drain channel 221. The flange 21 is convexly shaped and is arranged in a depression 114 that is correspondingly shaped and disposed on the inner side 111 of the top flexible sheet 10. The depression 114 may be preformed or may result fully or partially from the elasticity of the top flexible sheet 10. In this embodiment the dead volume of the flexible container 1 is further decreased, because in the completely drained state of the flexible container 1 the base plate 22 and the adjacent area 112 of the inner side 111 of the top flexible sheet 10 form an essentially smooth surface without gaps or protrusions at the interface 115 of the adjacent area 112 and the base plate 22. When the top flexible sheet 10 and the bottom flexible sheet 11 collapse, no dead volume remains between them.

Figure 5A:
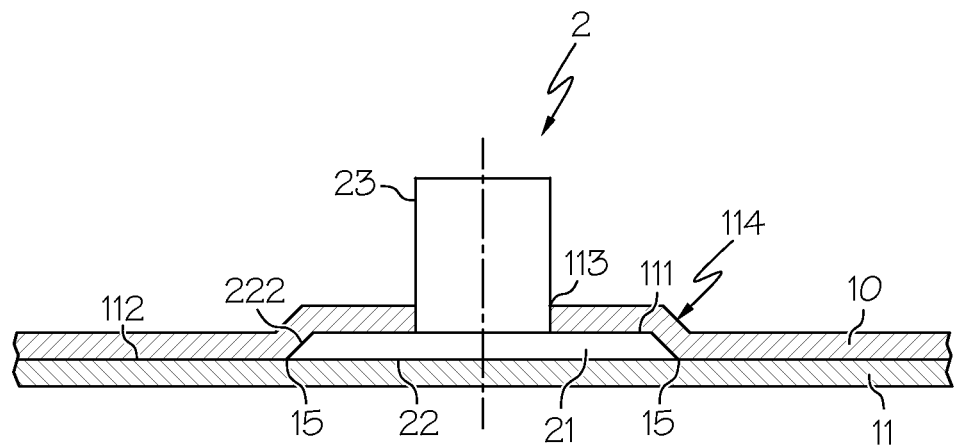
FIGS. 5A and 5B show schematic cross-sections of two other embodiments of a flexible container.
Figure 5B:
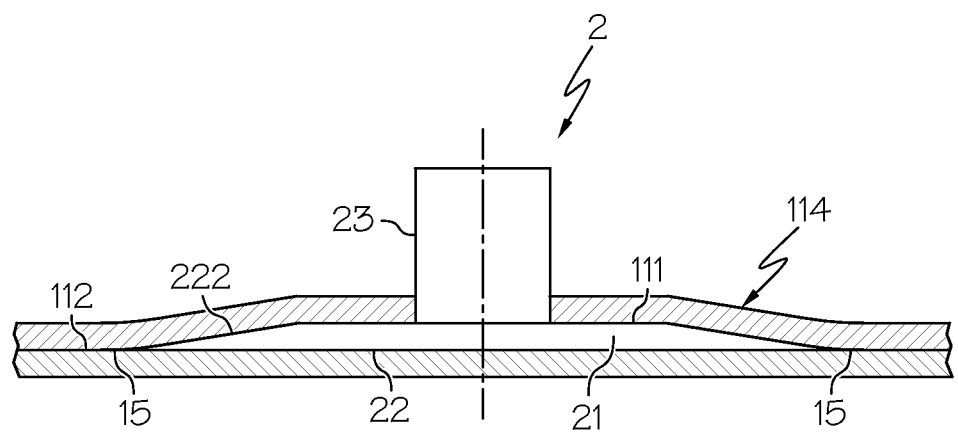

Two additional example embodiments of a port 2 are shown in FIGS. 5A and 5B to illustrate various contours of the flange 21. In these embodiments, as in the embodiment of FIG. 4A, the flange 21 is arranged in a depression 114 of the top flexible sheet 10. Adapter 23 protrudes through the port hole 113 in the top flexible sheet 10. In the embodiment shown in FIG. 5A, the edge 222 of the base plate 22 is relatively steep, compared with the same feature shown as elongated in FIG. 5B. In both embodiments, however, the base plate 22 and the adjacent area 112 of the inner side 111 of the top flexible sheet 10 form an essentially smooth and flat surface at the interface 115 when the flexible container 1 is empty. The depression 114 may be preformed or may result fully or partially from the elasticity of the top flexible sheet 10.

Figure 6A:
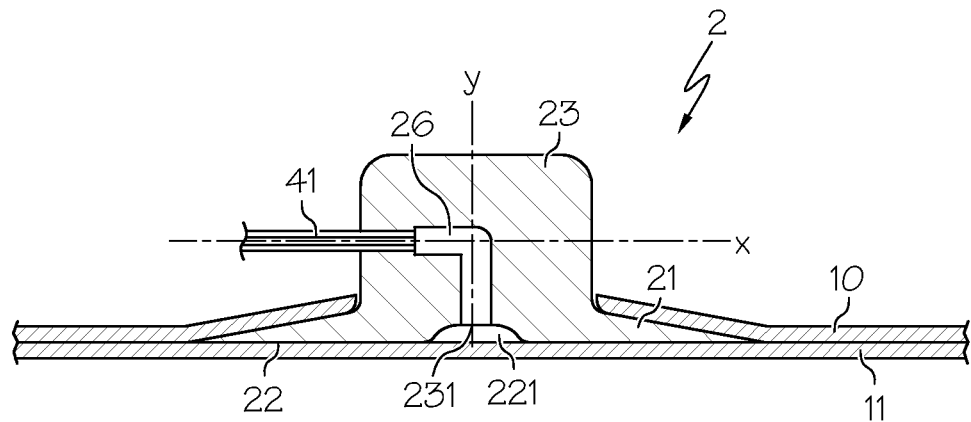
FIGS. 6A and 6B show schematic cross-sections of two further embodiments of a flexible container.
Figure 6B:
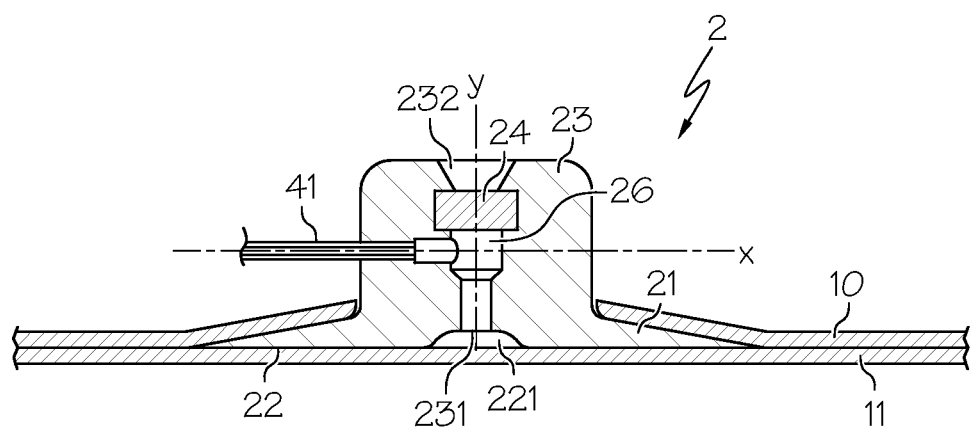

FIGS. 6A and 6B show two example embodiments of a port 2 in which an outer conduit system 41, for example of an infusion pump device (not shown), is directly connected to the inner conduit 26 of the port 2. The outer conduit system 41 is arranged such inner opening axis y (shown in FIGS. 6A and 6B as extending through the inner opening 231 and the inner conduit 26) is perpendicular to outer conduit system axis x (shown in FIGS. 6A and 6B as extending through the outer conduit system 41 and intersecting the inner opening axis y in the inner conduit 26) to reduce the overall device volume. The inner conduit 26 extends to the inner opening 231 and the drain channel 221. In the embodiment shown in FIG. 6B the outer conduit system 41 is combined with a septum 24. Furthermore, an outer opening 232 is present, through which the septum 24 may be accessed, for example, by a needle. A port 2 configured in this manner can be connected, for example, to an infusion pump device (not shown) in a space-saving manner via the outer conduit system 41, but may simultaneously be filled by a user with a syringe through the septum 24. In a further example embodiment not shown, a port may be connected to more than one outer conduit.

Figure 7:
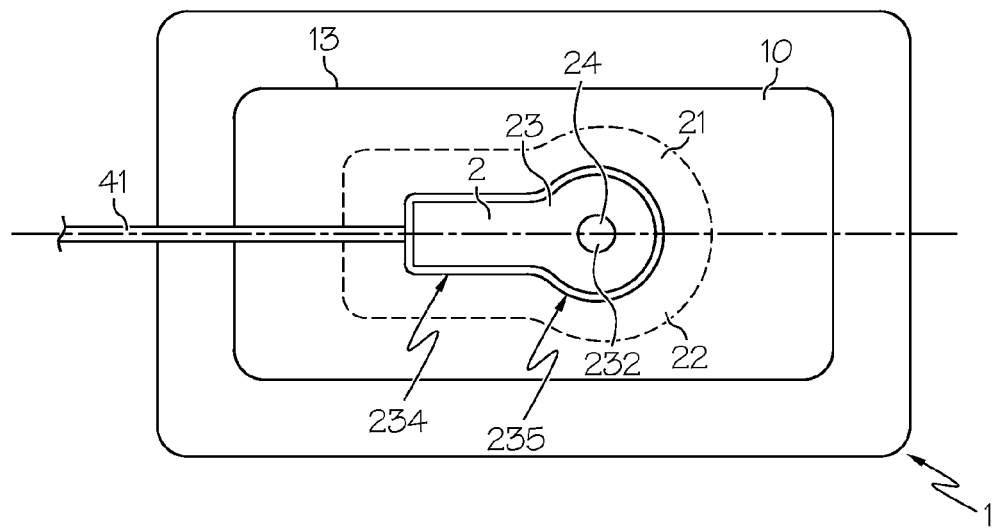
FIG. 7 shows a top view of a further embodiment of a flexible container.

Another example embodiment of a flexible container 1 is shown in FIG. 7, in a top view onto the flexible container 1 and the port 2. Also visible are the top flexible sheet 10, configured by way of illustration and not limitation as essentially rectangular, and the sealing rim 13. The port 2, with the adapter 23 and the base plate 22, is pear-shaped. An outer conduit system 41 leads to the thinner end 234 of the adapter 23. An outer opening 232 with a septum 24 inserted is visible on the circular part 235 of the adapter 23.

It will be understood that the port 2 need not be circular, but may have any suitable regular or irregular shape that provides the intended functionality. Furthermore instead of being arranged in the center of the flexible container 1 as shown in FIG. 7 and other figures, the port 2 may have any suitable position on the flexible container 1. In example embodiments not shown, the port 2 may be disposed near the sealing rim 13. Alternatively, the port 2 may be disposed partially inside and partially outside the sealing rim 13.

Figure 8:
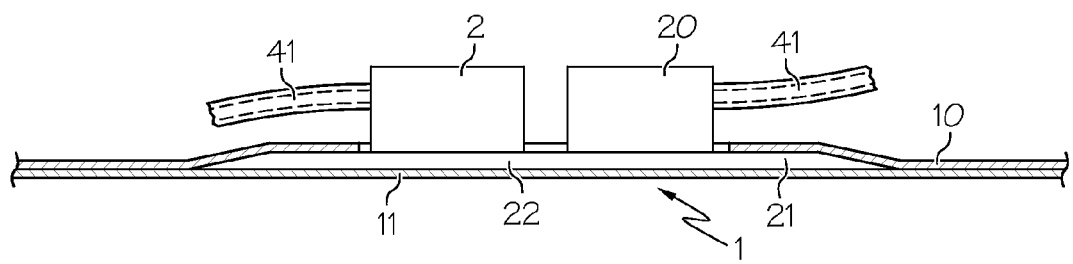
FIG. 8 shows a schematic cross-section of an embodiment of a flexible container having two ports that share a common base plate.

FIG. 8 shows an example embodiment of a flexible container 1 having a port 2 and an additional port 20, each connected an outer conduit system 41. The port 2 and the additional port 20 share a base plate 22 and a flange 21. It will be understood that the flexible container 1 is not limited to one or two ports but, rather, that the flexible container may comprise a plurality of separate ports. It will be understood that any number of ports may be combined into a unitary piece, such that each port comprises a unique adapter, but one or more ports share a common base plate, a common flange, or both, integral to the unique adapters of each port. Alternatively, each ports may be a unitary piece having its own adapter, flange, and base plate, all of which are integral to each other. The flexible container 1 additionally may contain ports for de-aerating the flexible container 1. In an example embodiment, a port of the flexible container is configured as an integral part of an infusion pump device.

An device for the automated release of a liquid medicament may comprise or incorporated at least one flexible container such as, for example, any of the flexible containers described in the example embodiments above. The device may be any appropriate medicine delivery device such as, for example, an infusion pump device.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

What is claimed is:

1. A flexible container for storing a medicament, the flexible container comprising:
   a top flexible sheet having at least one port hole defined therethrough;
   a bottom flexible sheet sealed to the top flexible sheet so as to form an inner storage volume between the top flexible sheet and the bottom flexible sheet; and
   at least one port having:
      a flange that is sealingly attached to an inner side of the top flexible sheet;

an adapter for connecting the port to a device and having an outer opening defined therein, the adapter extending from the flange and protruding through the at least one port hole in the top flexible sheet;

a base plate facing the inner storage volume and having an inner opening and at least one drain channel defined therein, the inner opening being disposed within the at least one drain channel;

an inner conduit defined therein extending from the inner opening to the outer opening so as to provide fluidic communication between the inner storage volume and the outer opening via the inner opening;

a septum disposed in a broad upper area of the inner conduit within the adapter and adjacent to the outer opening, the septum comprising a material able to reseal after being penetrated by an object; and an outer conduit system that connects the port to the device, the outer conduit system defining an outer conduit system axis that is perpendicular to an inner opening axis extending through the inner opening, wherein:

the flange, the adapter, and the base plate of the at least one port are integral to each other;

the at least one port is a unitary piece formed from a single continuous piece of material;

the at least one port is mounted within the flexible container only by the sealing attachment of the flange to the inner side of the top flexible sheet; and the outer conduit system is directly connected to the inner conduit of the port and the septum separates the inner conduit from the outer opening, whereby the port can be simultaneously filled through the septum while connected to the device.

2. The flexible container of claim 1, wherein the at least one drain channel extends from the inner opening to an outer edge of the base plate.

3. The flexible container of claim 1, wherein the base plate comprises a network of interconnected drain channels.

4. The flexible container of claim 1, wherein the at least one drain channel is a plurality of drain channels arranged in a manner selected from a star-like manner and a grid-like network.

5. The flexible container of claim 1, wherein the at least one drain channel is a plurality of linear drain channels and circular drain channels.

6. The flexible container of claim 1, wherein the at least one drain channel is a plurality of drain channels formed by a number of protrusions arranged on the base plate.

7. The flexible container of claim 1, wherein the inner conduit is an integral part of the inner opening.

8. The flexible container of claim 1, wherein the flange of the at least one port is disposed within a depression on an inner side of the top flexible sheet.

9. The flexible container of claim 1, wherein the base plate comprises a shape that defines an essentially flat and smooth surface along the base plate and an adjacent area of an inner side of the top flexible sheet.

10. The flexible container of claim 1, wherein the at least one port further comprises a bubble filter, a pressure sensor, a pressure-transfer membrane, a pumping mechanism, a component of any of these, or combinations thereof.

11. The flexible container of claim 1, wherein the at least one port is a pair of ports sharing a common base plate and a common flange.

12. The flexible container of claim 1, wherein the adapter of the at least one port comprises an inwardly deformed upper edge that grips the septum.

13. The flexible container of claim 1, wherein the flange comprises circumferentially arranged energy directors that direct energy when the flange is sealingly attached to the inner side of the top flexible sheet by ultrasonic welding.

14. A port for a flexible container that is used with a device and has walls for storing a medicament there between, the port comprising:

a flange which connects to an inner side of one of the walls;

an adapter for connecting the port to the device and having an outer opening defined therein, the adapter extending perpendicularly from the flange;

a septum disposed in a broad upper area of the inner conduit within the adapter and adjacent to the outer opening, the septum comprising a material able to reseal after being penetrated by an object;

a base plate extending from the flange and having an inner opening and at least one drain channel defined therein, the inner opening being disposed within the at least one drain channel; and an outer conduit system that connects the port to the device, the outer conduit system defining an outer conduit system axis that is perpendicular to an inner opening axis extending through the inner opening, wherein:

the port has an inner conduit defined therein, the inner conduit extending from the inner opening to the outer opening;

the adapter comprises an inwardly deformed upper edge that grips the septum;

the flange, the adapter, and the base plate are integral to each other;

the port is a unitary piece formed from a single continuous piece of material; and the outer conduit system is directly connected to the inner conduit of the port and the septum separates the inner conduit from the outer opening, whereby the port can be simultaneously filled through the septum while connected to the device.

15. The port of claim 14, wherein the at least one drain channel extends from the inner opening to an outer edge of the base plate.

16. The port of claim 14, wherein the base plate comprises a network of interconnected drain channels.

17. The port of claim 14, wherein the port further comprises a bubble filter, a pressure sensor, a pressure-transfer membrane, a pumping mechanism, a component of any of these, or combinations thereof.

18. A device for the automated release of a medicament, the device comprising at least one flexible container according to claim 1.

19. The device of claim 18, wherein the device comprises an infusion pump.

* * * * *

UNITED STATES PATENT AND TRADEMARK OFFICE
CERTIFICATE OF CORRECTION

PATENT NO.       : 8,734,396 B2
APPLICATION NO.  : 12/604519
DATED            : May 27, 2014
INVENTOR(S)      : Martin Wyss Page 1 of 2

It is certified that error appears in the above-identified patent and that said Letters Patent is hereby corrected as shown below:

In the Specification

Col. 1, Line 62,
  "separate, smaller housings that can joined by a wireless or a" should read
  --separate, smaller housings that can be joined by a wireless or a--;

Col. 5, Line 14,
  "Further, the term needle defines a piercing member (including" should read
  --Further, the term "needle" defines a piercing member (including--;

Col. 8, Line 35,
  "injection molding, a septum may be placed within in the" should read
  --injection molding, a septum may be placed within the--;

Col. 9, Line 56,
  "is arranged such inner opening axis y (shown in FIGS. 6A and" should read
  --is arranged such that inner opening axis y (shown in FIGS. 6A and--;

Col. 10, Line 26,
  "connected an outer conduit system 41. The port 2 and the" should read
  --connected to an outer conduit system 41. The port 2 and the--;

Col. 10, Line 35,
  "tively, each ports may be a unitary piece having its own" should read
  --tively, each port may be a unitary piece having its own--;

Col. 10, Line 41,
  "An device for the automated release of a liquid medicament" should read
  --A device for the automated release of a liquid medicament--; and Signed and Sealed this
Thirty-first Day of March, 2015

Michelle K. Lee
*Director of the United States Patent and Trademark Office*

Col. 10, Line 42,

"may comprise or incorporated at least one flexible container" should read
--may comprise or incorporate at least one flexible container--.